United States Patent

Kauhaniemi et al.

Patent Number: 6,159,424
Date of Patent: *Dec. 12, 2000

[54] APPARATUS FOR TAKING SAMPLES

[75] Inventors: Ilpo Kauhaniemi, Tampere; Pekka Heinonen; Harri Okkonen, both of Espoo, all of Finland

[73] Assignee: Nokia Mobile Phones, Ltd., Espoo, Finland

[*] Notice: This patent issued on a continued prosecution application filed under 37 CFR 1.53(d), and is subject to the twenty year patent term provisions of 35 U.S.C. 154(a)(2).

[21] Appl. No.: 09/097,339

[22] Filed: Jun. 15, 1998

[30] Foreign Application Priority Data

Jun. 19, 1997 [FI] Finland ................................ 972634

[51] Int. Cl.⁷ .................................................. G01N 35/00
[52] U.S. Cl. ............................. 422/63; 422/65; 436/46
[58] Field of Search ............................... 436/46; 422/58, 422/61, 63, 65

[56] References Cited

U.S. PATENT DOCUMENTS

| | | | |
|---|---|---|---|
| 3,497,320 | 2/1970 | Blackburn | 436/46 |
| 4,218,421 | 8/1980 | Mack, Jr. et al. | 422/66 |
| 4,224,032 | 9/1980 | Glover et al. | 436/46 |
| 4,328,184 | 5/1982 | Kondo | 422/58 |
| 4,894,347 | 1/1990 | Hillyard et al. | 422/61 |
| 5,169,787 | 12/1992 | Knappe et al. | 436/169 |
| 5,329,686 | 7/1994 | Kildal et al. | 29/450 |
| 5,424,035 | 6/1995 | Hones et al. | 422/55 |
| 5,971,941 | 10/1999 | Simons et al. | 600/573 |

FOREIGN PATENT DOCUMENTS 42 34 553 A1  4/1993  Germany.

*Primary Examiner*—Lyle A. Alexander
*Attorney, Agent, or Firm*—Perman & Green, LLP

[57] ABSTRACT

The invention relates to an apparatus (5) for handling measurement strips (1) needed for taking liquid samples, such as blood samples, the measurement strips having porous material for absorbing and analyzing a liquid sample. The apparatus (5), according to the invention, is formed of a store (6) of measurement strips that receive samples, the store having a compound construction, a store (7) of used measurement strips and a measurement strip feeding mechanism (8,9). The apparatus has preferably been integrated into a casing, which can be connected as part of a mobile phone or a corresponding device.

11 Claims, 4 Drawing Sheets

APPARATUS FOR TAKING SAMPLES

FIELD OF THE INVENTION

This invention relates to an apparatus for taking samples. The invention relates particularly to an apparatus for handling measurement strips needed for taking liquid samples, such as blood samples. The invention is related to the handling of such measurement strips that have a gauze dressing, made of porous material, or a corresponding pad for absorbing and optically analysing a liquid sample. These types of measurement strips are used, amongst other things, for the repeated monitoring of a patient's blood quality, e.g., for the monitoring of the glucose content of the blood of a diabetic patient or the measuring of the blood's cholesterol content, which can be defined optically on the basis of the colour of a transilluminating or reflecting ray of light. The invention also relates to the measurement strips used in the apparatus.

BACKGROUND OF THE INVENTION

Different types of apparatuses are known that make blood analyses swiftly and reliably. For example, the skin is lanced by means of a small, spring-mounted lancet, and the drop of blood from the skin is absorbed into a small, gauze dressing-like pad. The gauze dressing is normally attached to the centre of a narrow piece of plastic forming a so-called strip. In the plastic strip, there is a hole covered with a transparent or coloured film that penetrates light, whereto light is directed. By using a suitable strip and a calculation model, it is possible to define accurately, on the basis of the reflected colour, the blood property monitored each time, e.g., the glucose or cholesterol content.

A disadvantage of the apparatuses in question, particularly in long-term use, is that the measurements must be taken where the apparatuses are located, i.e., at home, at a workplace or at the doctor's. For example, for a diabetic, who has accurate medication times directly dependent on the glucose content of the blood, this is an impediment to a freedom of movement and living.

SUMMARY OF THE INVENTION

The object of the present invention is to produce such an apparatus for the handling of the measurement strips needed for taking liquid samples that can be carried with and easily used everywhere. It is characteristic of an apparatus, according to the invention, that it comprises a store for unused measurement strips, a store of used measurement strips and a measurement strip feeding mechanism. It is characteristic of the measurement strip, according to the invention, that it comprises a frame, surrounding the sample material level with its surface area, that exceeds the surface of the sample material perpendicularly in relation to said surface area forming an edge surrounding the sample material.

The apparatus, according to the invention, has many advantages. The handling of individual strips ends and it is possible to place, in the store of the apparatus, a number of strips equivalent to at least one week's need, depending on the case and as necessary. A user of the apparatus can carry it with him and use it wherever he goes, i.e., the user no longer has to go to a specific place for a test. The measurement strip, according to the invention, provides for the measurement strips to be packed in a small space in a pile and it also enables a measurement strip to be easily handled by means of an apparatus according to the invention.

The other preferred embodiments of the invention are characterised in what has been presented later in the claims.

BRIEF DESCRIPTION OF THE DRAWINGS

In the following, the invention will be discussed in detail with the help of examples by referring to the enclosed drawings, of which

DETAILED DESCRIPTION

Figure 1A:
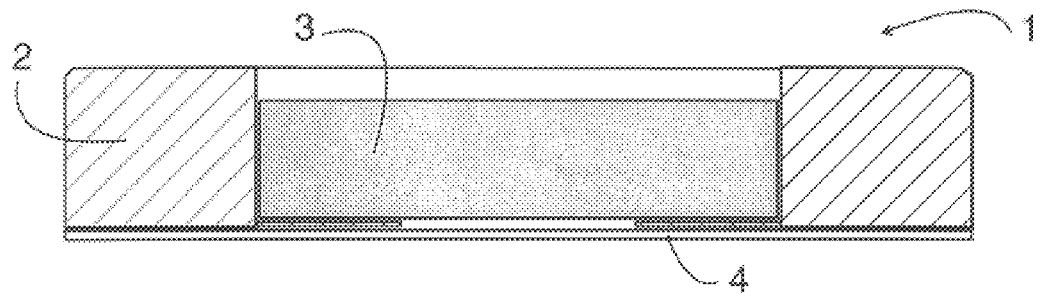
FIGS. 1a and 1b illustrate an example of a measurement strip, according to the invention, as a cross-section and in perspective.
Figure 1B:
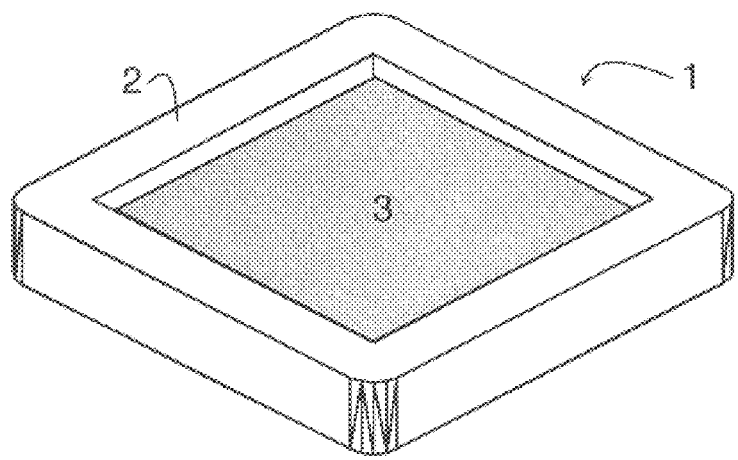
Figure 2:
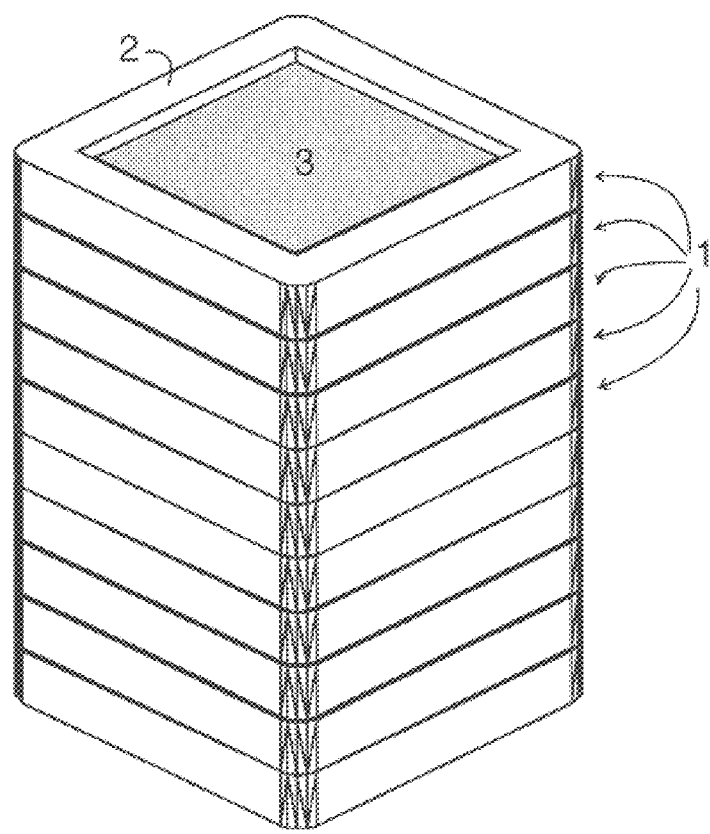
FIG. 2 illustrates measurement strips, according to FIG. 1, when piled.

FIG. 1a illustrates a measurement strip, according to the invention, for use in an apparatus, according to the invention, in this exemplary case, a measurement strip 1, in the shape of a square, as a cross-section. It is essentially formed of three parts; a plastic frame 2, a hydroscopic sample pad 3, made of a porous material, and a transparent plastic film 4 on the bottom. The frame can be approx. 1–2 mm thick, and the size of the sample pad is, e.g., 8 mm×8 mm. The frame 2 of the measurement strip comes slightly above the surface of the sample pad 3, whereupon the frame edge 2 protects the sample pad when the measurement strips are piled. On the lower edge of the frame, there is a thin projection which supports and protects the sample pad from below. The plastic film 4 can be either colourless or coloured for producing a reflecting ray of light of a required colour when analysing the sample. FIG. 1b illustrates a measurement strip as a perspective. The measurement strips can be piled one on top of the other as illustrated in FIG. 2. Using the construction illustrated in FIGS. 1 and 2, the measurement strip can be made small in size, easy to pile, as well as durable.

Figure 3:
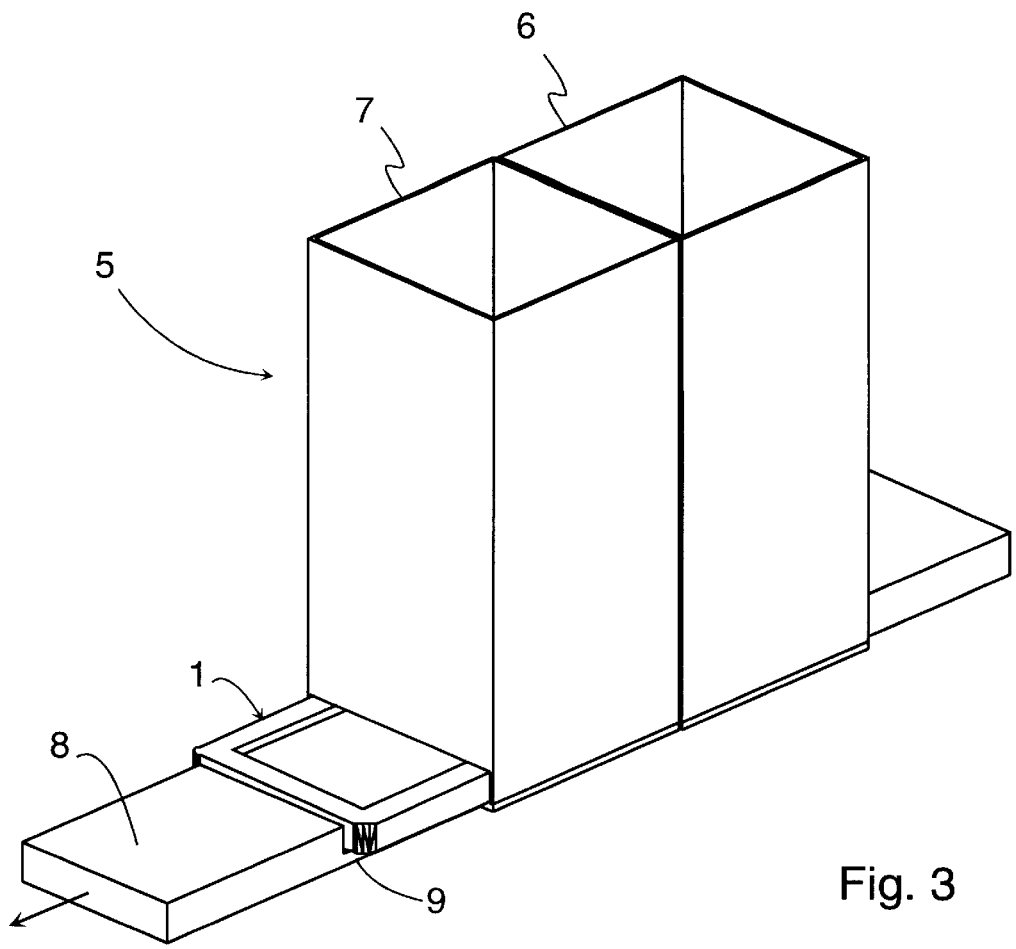
FIG. 3 illustrates a diagrammatic perspective of an embodiment of an apparatus according to the invention.

FIG. 3 illustrates a storage device 5 according to the invention. The apparatus is formed of adjacent storage boxes 6 and 7, as well as of a slide 8 which closes one end of the boxes and can be moved in relation to them. The box 6, containing unused measurement strips, has been arranged to surrender one measurement strip 1 into a recess 9, of a corresponding size, of the slide 8 when the slide is in its extreme position, i.e., directly below the box 6. When the slide has been drawn to its other extreme position, in the direction indicated by the arrow, the measurement strip 1 has passed the storage box 7, containing used measurement strips, and is at an analysing station (see FIG. 4d). Naturally, the location of the analysing station may be other than underneath the box 7. A diabetic patient's average weekly sampling need is 15 times which means that, in the box 6, there is a pile of at least 15 measurement strips, preferably about 25 pieces which is a sufficient number for the weekly needs of even the more active user.

Figure 4A:
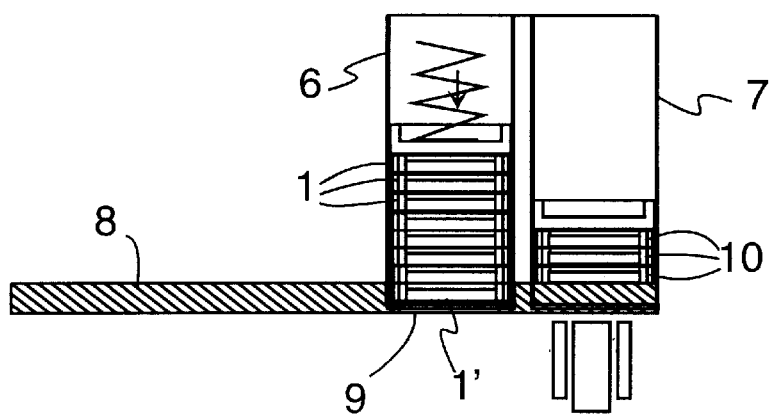
FIGS. 4a–4f illustrate an operating sequence of an apparatus, according to FIG. 3.
Figure 4B:
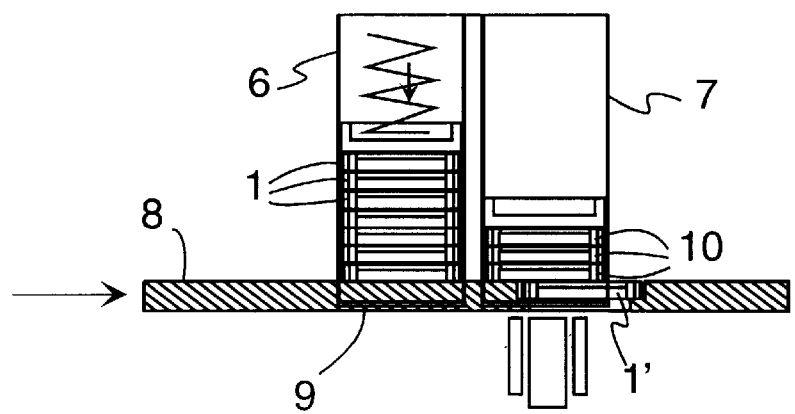
Figure 4C:
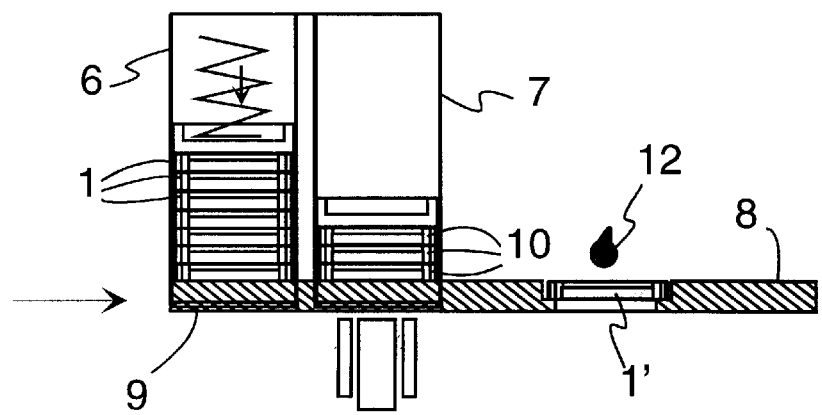

FIGS. 4a–4f illustrate how the feeding of new measurement strips for analysis and the returning of used strips into the storage box can be implemented. FIG. 4a illustrates a storage and feeding device, according to FIG. 3, wherein unused measurement strips 1 are stored in a pile in the storage box 6, used measurement strips 10 are stored in a pile in the box 7 and wherein one new measurement strip 1' has been transferred into the recess 9 of the slide 8 by means of a spring located in the box 6. When the slide 8 is moved slightly in the direction of the arrow, the situation is as illustrated in FIG. 4b, where the measurement strip 1' is passing the box 7. Unused strips remain in the box 6, because the recess in the slide 8, receiving them, is no longer underneath the box. The same applies to the box 7, because the recess 9 only has space for one measurement strip at a time. When the slide 8 has been transferred to its extreme position (FIG. 4c), a liquid sample, e.g., a drop of blood 12, is dropped on the sample pad of the measurement strip 1'.

Figure 4D:
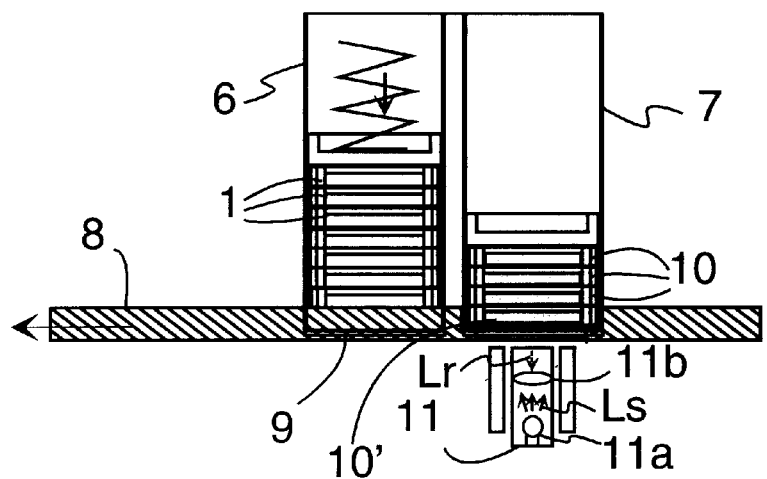

When the slide is drawn back in the direction of the arrow, as illustrated in FIG. 4d, its recess 9 now contains a measurement strip 10' containing a sample to be analysed. The analysis is carried out when the measurement strip 10' and the recess 9 are located directly below the box 7 on an analysing apparatus 11 arranged there, which can be formed, e.g., of a source of light 11a, having a standard construction, for transmitting a light Ls for illuminating the sample pad of the measurement strip and of a detector 11b of a reflected light Lr. The analysing apparatus and method are not described here in more detail.

Figure 4E:
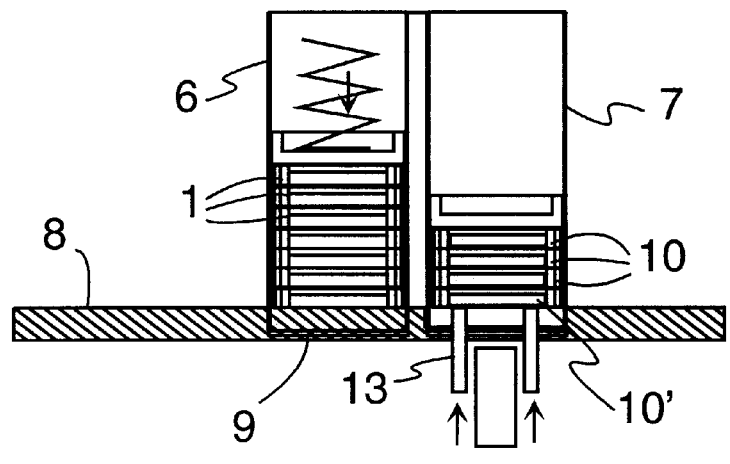
Figure 4F:
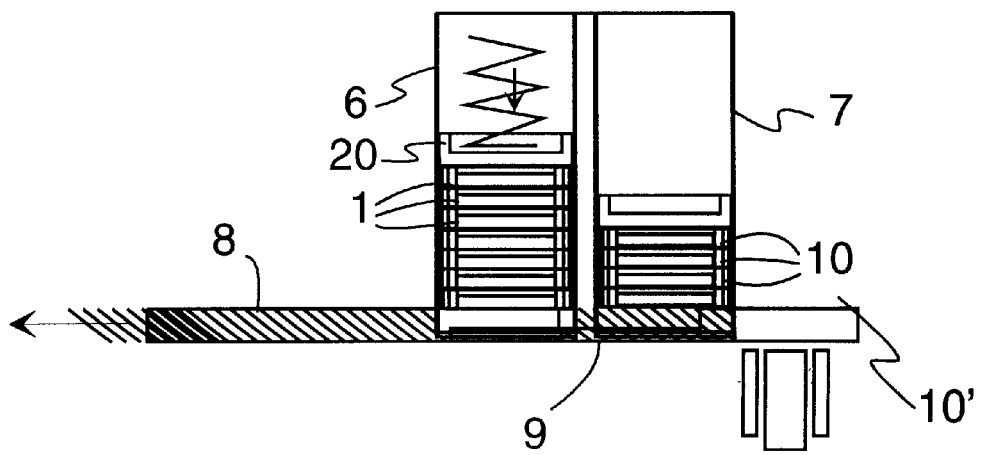

After analysing, the measurement strip 10' is transferred into the box 7 for used measurement strips, as illustrated in FIG. 4e, by pushing a device pusher 13 upwards. At the foot of the box 7, there are flexible claws which the device pusher 13 temporarily moves aside in order to let the measurement strip in the box. When the device pusher moves back to its lower position, the claws return and hold the used measurement strips 10 in the box 7. Alternatively, at the foot of the box 7, there can be flexible holders which, in the figure, yield upwards but not downwards. In this case, when the device pusher 13 pushes the used measurement strip 10' upwards, the holders let the measurement strip through, but prevent it from dropping downwards. The boxes 6 and 7, having a compound construction, are removed after the box 7 has become full, whereupon the box 6 is correspondingly empty. A corresponding transfer and claw construction can also be considered for the box 6 although, in this case, the construction becomes somewhat more complex.

When the slide is taken further back to its other extreme position (FIG. 4f), we return to the initial situation illustrated in FIG. 4a. A bottom 20 of the box 6 for unused strips is preferably of silica gel, in which case, possible moisture is absorbed by it and not by the hydrostatic sample pads 3 of unused strips. Alternatively, a separate silica gel capsule is arranged inside the box nearest to the bottom (in place of the last measurement strip).

Figure 5:
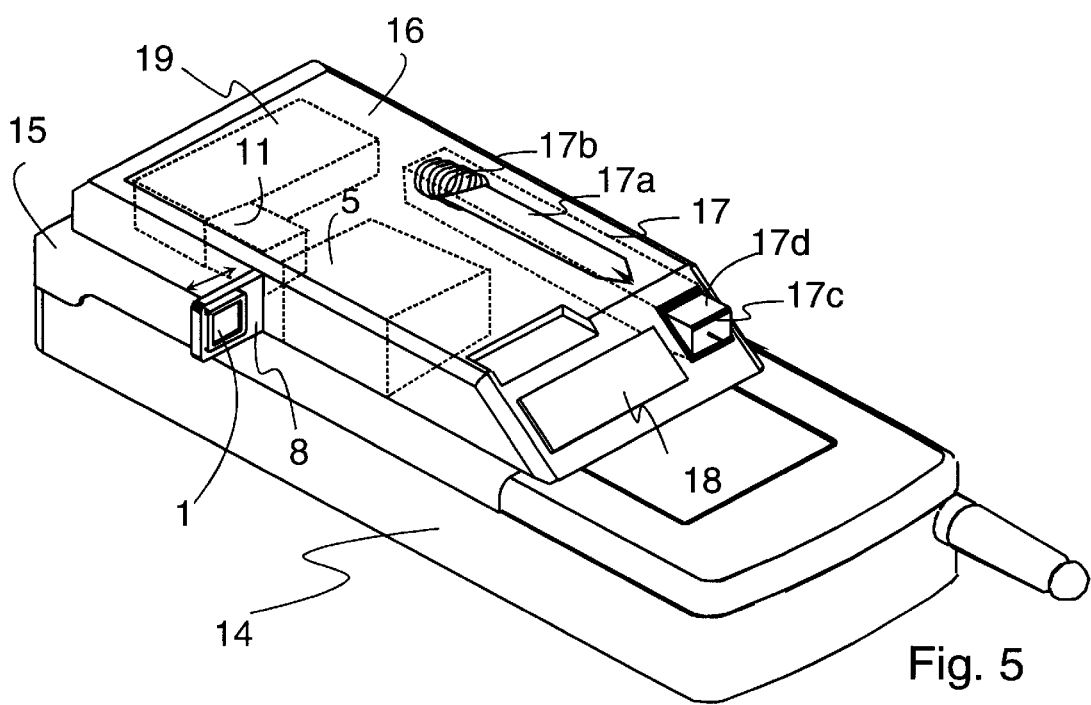
FIG. 5 illustrates an apparatus, according to the invention, connected to a mobile phone.

FIG. 5 illustrates an apparatus 5, according to the invention, connected as part of a mobile phone 14 so that it has been placed in a separate analysing unit 16 on top of a battery pack 15 of the mobile phone or it has been integrated in some other way in connection with the battery pack. Thus, the invention also relates to a unit wherein, in addition to a storage device, also other means needed for taking liquid samples, such as blood samples, have been integrated into the same pack. All the means needed for analysing have been integrated into a compact portable analysing unit 16 (to be kept, e.g., in the hand or pocket) containing the measurement strip storage and feeding device 5, a lancet 17 for lancing the skin for taking a blood sample, the analysing device 11 (see FIG. 4d) and a display 18 for presenting the results of the analyses. Both the mobile phone 14 and the analysing unit 16 get the required energy from the battery 15.

Alternatively, the analysing unit 16 may contain in itself batteries of a mobile phone, in which case, it is connected in the place of the mobile phone's battery case to replace the mobile phone's battery packet. In this case, both the mobile phone 14 and the analysing unit 16 get the required energy from the batteries included in the analysing unit. In both cases, the user of the apparatus, according to the invention, can easily carry it with him wherever he goes.

In the case, illustrated in FIG. 5, the analysing unit 16 is used so that the lancet 17 is set (e.g., by a button located at the edge of the analysing unit, not shown in the figure), a finger is set on the lancet, whereupon a needle 17a of the lancet lances the skin when the lancet is released (e.g., by the same button). The needle 17a penetrates, preferably by means of a spring force 17b, with a quick straight movement forwards through a hole 17c and lances the skin. A hatch 17d of the lancet 17 can be opened to replace the needle 17a. Alternatively, the bottom of the analysing unit 16 opens on a hinge at the end of an electronics unit 19 of the analysing device, whereupon new boxes 6 and 7, as well as a new needle can be replaced through it. It is also possible to arrange a hatch at the point of the mere storage device 5 for replacing the boxes.

Normally, the slide 8 is located inside the analysing unit so that only the outer edge of the slide is shown on the level of the edge of the analysing unit. By pushing the slide 8 inwards or some other button (not shown), the slide 8 and its measurement strip 1 slide forth as illustrated in the figure (e.g., with the help of a spring force arranged at the other end of the slide). A drop of blood from the skin, lanced by the lancet, is placed on the measurement strip 1 and the slide is pushed back into the apparatus, i.e., inside the analysing unit 16, whereupon the source of light 11a, inside the analysing device 11 (FIG. 4d), transmits the ray of light Ls on to the underside of the measurement strip, wherefrom it is reflected Lr back on to the detector or photosensor 11b located in the analysing device.

The electronics 19 of the analysing device carry out programmably the blood analysis by methods known as such. The result of the analysis is presented on the display 18, controlled by the electronics 19.

FIG. 5 illustrates a compact analysing unit for a patient, wherein measurement strips, a lancet and an analysing device have been connected to the same unit. Thus, the patient can easily carry with him all the necessary means. In the example, illustrated in FIG. 5, the unit 16 has been arranged to be connected to a mobile phone so that it can be easily carried with under cover of the mobile phone. The connection to a mobile phone enables the results of the analyses to be sent through a mobile telephone network using the mobile phone.

This paper presents the implementation and embodiments of the present invention with the help of examples. It is obvious to a person skilled in the art that the present invention is not restricted to details of the embodiments presented above, and that the invention can also be implemented in another form without deviating from the characteristics of the invention. The embodiments presented above should be considered illustrative, but not restricting. Thus, the possibilities of implementing and using the invention are only restricted by the enclosed claims. Consequently, the various options of implementing the invention as determined by the claims, including the equivalent implementations, also belong to the scope of the invention.

What is claimed is:

1. A portable apparatus for handling measurement strips needed for taking liquid samples, the measurement strips having liquid absorbing material for absorbing a liquid sample, the apparatus comprising first and second elongate storage boxes having first and second ends, respectively, in side by side immediately adjoining relationship, the first storage box adapted to store unused measurement strips in a first upright stack, the second storage box adapted to store used measurement strips in a second upright stack to temporarily retain them for subsequent sanitary disposal and a measurement strip feeding mechanism for transporting measurement strips from the second end of the first storage box to the second end of the second storage box, one by one, via a position at which the measurement strips receive the liquid samples, the second ends, respectively, of the first and second storage boxes being in immediately adjoining relationship.

2. An apparatus, according to claim 1, wherein the measurement strips are essentially formed of frames, in the shape of a square or a rectangle, inside of which an absorbent material for absorbing and analysing a liquid sample has been placed.

3. An apparatus, according to claim 1, wherein the feeding mechanism of the measurement strips is formed of a slide closing one end of the adjacent storage boxes and moving in relation to them, in a recess of which the box, containing the unused measurement strips, has been arranged to surrender one measurement strip, when the slide is in its extreme position, and that the measurement strip has been arranged to receive a sample, when the slide is in its other extreme position, and that the measurement strip, containing the sample, has been arranged for being analysed and fed from said recess into the box, containing used measurement strips, when the slide is in a position between said two extreme positions.

4. An apparatus, according to claim 1, wherein the apparatus has been integrated into a casing, which can be connected as part of a mobile phone or a corresponding device.

5. An apparatus, according to claim 1, wherein, in addition, it comprises, in the same casing, a sample analysing apparatus, as well as a lancet for lancing the skin for taking a blood sample.

6. A portable apparatus according to claim 1 wherein the fist store has an open first end and a second end distant therefrom; wherein the second store has an open first end adjacent the first end of the first store and a second end distant therefrom adjacent the second end of the first store; and wherein the measurement strip feeding mechanism is operable for transporting measurement strips from the second end of the first store to the second end of the second store.

7. A portable apparatus according to claim 1 wherein the portable apparatus includes an analyzing unit for analyzing a chemical imparted to the measurement strip.

8. A portable apparatus according to claim 7 wherein the chemical imparted to the measurement strip is in a body fluid and wherein the measurement strip feeding mechanism is operable for transporting the measurement strip from a body fluid receiving position to an analysis position to the second store.

9. A portable apparatus according to claim 7 wherein blood is imparted to the measurement strip and wherein the measurement strip feeding mechanism is operable for transporting the measurement strip from a blood receiving position to an analysis position to the second store.

10. A portable storage device for storing measurement strips needed for taking liquid samples, the measurement strips having liquid absorbing material for absorbing a liquid sample, the device comprising a first store for storing unused measurement strips in a first pile, a second store for storing used measurement strips in a second pile the first and second stores being in immediate adjacent relationship and a measurement strip feeding mechanism for transporting the measurements strips, the measurement strips being transportable from the first store to the second store via a position at which the measurement strips receive the liquid sample.

11. A portable apparatus for handling measurement strips needed for taking liquid samples, the measurement strips having liquid absorbing material for absorbing a liquid sample, the apparatus comprising a first storage box for storing unused measurement strips in a first upright stack, a second storage box for storing used measurement strips to a second upright stack, the first and second storage boxes being in side by side immediately adjoining relationship, the storage boxes having first and second ends, respectively, the second ends being in immediately adjoining relationship, a measurement strip feeding mechanism for transporting measurement strips from the second end of the first storage box to the second end of the second storage box via a position at which the measurement strips receive the liquid samples and an analyzing unit for analyzing the liquid samples to produce analysis results, the portable apparatus being used in combination with a mobile phone, the mobile phone being used to transmit the analysis results through a mobile telephone network.

* * * * *